United States Patent [19]

Bernstein et al.

[11] Patent Number: 5,736,535
[45] Date of Patent: Apr. 7, 1998

[54] 1-PYRIMIDINYLACETAMIDE COMPOUNDS WHICH ARE INHIBITORS OF HUMAN LEUKOCYTE ELASTASE

[75] Inventors: Peter Robert Bernstein, Wallingford; Philip Duke Edwards, Kennet Square; Andrew Shaw, Kennett Square, all of Pa.; Ashokkumar Bhikkappa Shenvi, Wilmington, Del.; Royston Martin Thomas, Macclesfield, England; Chris Allan Veale, Newark, Del.; Peter Warner, Macclesfield, England; Donald John Wolanin, Orange, Conn.

[73] Assignee: Zeneca Limited, United Kingdom

[21] Appl. No.: 375,136

[22] Filed: Jan. 19, 1995

Related U.S. Application Data

[63] Continuation of Ser. No. 44,855, Apr. 8, 1993, abandoned.

[30] Foreign Application Priority Data

Apr. 16, 1992 [GB] United Kingdom ............ 9208382
Aug. 14, 1992 [GB] United Kingdom ............ 9217301

[51] Int. Cl.$^6$ .................. A61K 31/69; C07F 5/02; C07F 5/04
[52] U.S. Cl. .................. 514/64; 544/69; 544/229
[58] Field of Search .................. 544/69, 229; 514/64

[56] References Cited

U.S. PATENT DOCUMENTS

| | | | |
|---|---|---|---|
| 4,499,082 | 2/1985 | Shenvi et al. | 514/2 |
| 4,537,773 | 8/1985 | Shenvi | 514/63 |
| 4,910,190 | 3/1990 | Bergerson et al. | 514/19 |
| 4,963,655 | 10/1990 | Kinder et al. | 530/331 |
| 5,169,841 | 12/1992 | Kleeman et al. | 514/63 |
| 5,254,558 | 10/1993 | Bernstein et al. | 514/269 |

FOREIGN PATENT DOCUMENTS

| | | |
|---|---|---|
| 0 315 574 | 5/1989 | European Pat. Off. . |
| 0 471 651 A2 | 2/1992 | European Pat. Off. . |
| 0 509 769 A2 | 10/1992 | European Pat. Off. . |
| 0 528 633 A1 | 2/1993 | European Pat. Off. . |

OTHER PUBLICATIONS

Drug Evaluations by American Medical Association pp. 509–510 (1993).

*Primary Examiner*—Emily Bernhardt
*Attorney, Agent, or Firm*—Liza D. Hohenschutz

[57] ABSTRACT

The present invention relates to certain novel substituted derivatives which are 1-pyrimidinylacetamide derivatives of formula I,

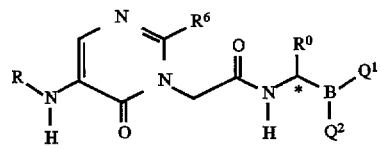

which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these substituted derivatives, processes for preparing the substituted derivatives, pharmaceutical compositions containing such substituted derivatives and methods for their use.

11 Claims, No Drawings

1-PYRIMIDINYLACETAMIDE COMPOUNDS WHICH ARE INHIBITORS OF HUMAN LEUKOCYTE ELASTASE

This is a continuation of application Ser. No. 08/044,855 filed on Apr. 8, 1993, now abandoned.

The present invention relates to certain substituted derivatives, in particular, certain 1-pyrimidinylacetamide compounds, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also includes intermediates useful in the synthesis of these substituted derivatives, processes for preparing the substituted derivatives, pharmaceutical compositions containing such substituted derivatives and methods for their use.

In U.S. Pat. No. 4,499,082, of 12 Feb. 1985, assigned to E. I. DuPont De Nemours and Company, there is disclosed a series of peptidyl boronic acid derivatives as reversible inhibitors of proteolytic enzymes, including HLE. It is well known that boronic acid derivatives, such as for example the a corresponding esters, readily may be hydrolyzed under the in vitro and in vivo conditions in which they are tested and used. In U.S. Pat. No. 4,910,190, of 20 Mar. 1990, assigned to ICI Americas Inc. (now ZENECA Inc.), there is disclosed a series of peptidoyl trifluoromethane ketone derivatives which are HLE inhibitors. Disclosed herein is a series of substituted 2-(6-oxo-1,6-dihydro-1-pyrimidinyl)-N-[3,3-difluoro-1-(lower alkyl)-2-oxo-3-(boronic acid residue)propyl]acetamide derivatives, which unexpectedly possess inhibitory properties against HLE, which provides the basis for the present invention.

According to the invention there is provided a Compound of the invention which is a compound of formula I (formula set out, together with other formulae referred to by Roman numerals, following the Examples) wherein:

$R^0$ is (1–5C)alkyl;

R is hydrogen; or

R is an acyl group of formula A.X.CO— in which A.X—, taken together, is hydrogen, trifluoromethyl, 2,2,2-trifluoroethoxy, amino, methoxyamino, 2,2,2-trifluoroethylamino, RbRcN.O—, RaOCONH—, $R^1SO_2NH$—, RaOCO—, RbRcNCO— or RaCO—; or R is an acyl group of formula A.X.CJ— in which J is oxygen or sulfur;

X is a direct bond, imino, oxy or thio; and

A is as defined below or

A is tetrahydropyran-4-yl, 1-methylpiperid-4-yl, or 5-methyl-1,3-dioxacyclohex-5-ylmethyl; or R is a sulfonyl group of formula $D.W.SO_2$— in which D.W—, taken together, is hydroxy, amino, di(lower alkyl)amino, 2,2,2-trifluoroethylamino, 2,2,2-trifluoroethyl, 3,3,3-trifluoropropyl or trifluoromethyl; or W is a direct bond, imino, carbonylimino, oxycarbonylimino or iminocarbonylimino; and D is as defined below; or R is a group G as defined below;

The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)-alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, $CH_2COORa$, CONRbRc, $CH_2CONRbRc$, $COO(CH_2)_2NReRf$, cyano, $SO_2R^1$, $CONRdSO_2R^1$, NReRf, NRgCHO, $NRgCOR^2$, $NRgCOOR^2$, NRhCQNRiRj, $NRkSO_2R^3$, $SO_2NRlRm$, $SO_2NRnCOR^4$ and $P(O)(ORa)_2$ in which Q is oxygen or sulfur;

Ra–Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$—$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl;

$R^6$ is (1–5C)alkyl which has no tertiary carbon, (3–7C) cycloalkyl, aryl or heteroaryl, which aryl or heteroaryl independently may bear one or more of the substituents defined for the group A or an aryl or heteroaryl moiety thereof;

$Q^1$ and $Q^2$, which may be the same or different, is each hydroxy or $OR^7$, or when taken together form a moiety derived from a physiologically acceptable dihydroxy compound having at least two hydroxy groups separated by at least two connecting atoms in a chain or ring, said chain or ring comprising carbon atoms, and optionally, a heteroatom or atoms which can be O, S or N, wherein $R^7$ is (1–10C) alkyl, (3–10C)cycloalkyl, benzyl or phenyl in which benzyl or phenyl the ring may bear one or more halogeno, lower alkyl or lower alkoxy substituents; and provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote both straight and branched groups; but reference to an individual radical such "propyl" embraces only the straight chain ("normal") radical, a branched chain isomer such as "isopropyl" being specifically referred to. Lower alkyl and lower alkoxy refer to radicals containing one to four carbon atoms. Lower acyloxy refers to a radical containing one to five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^o$ is isopropyl, a compound of formula I may be viewed as a valyl (or "borovaline") derivative. In general, a compound of formula I having the (S)-configuration at the chiral center indicated by "*" which corresponds to the L-alanyl configuration, is preferred. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the epimerization of the chiral center indicated by "*" in formula I, it may be preferred to utilize a compound of formula I as a mixture of the (S)- and (R)-isomers at the center indicated by "*" in formula I.

A compound of formula I may exhibit polymorphism. The compound may form solvates. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

It is preferred that the radicals $R^o$, R and $R^6$ not contain nor introduce an additional element of chirality into the molecule beyond the chiral center indicated by "*" in formula I; however, it may be preferred that the boron substituents $Q^1$ and $Q^2$ be chiral.

Particular values are listed below for radicals, substituents and ranges for illustration only and they do not exclude other defined values or other values within defined ranges for the radicals and substituents.

A particular value for $R^o$ is methyl, ethyl, propyl, isopropyl or isobutyl.

A particular value for W is a direct bond or imino.

A particular value for G is (1–3C)alkyl, aryl(1-C)alkyl or heteroaryl(1–2C)alkyl which may bear one or more substituents as defined above for G or a part thereof.

A particular value of (1–6C)alkyl is methyl, ethyl, propyl, isopropyl, butyl, isobutyl, t-butyl, pentyl, 3-methylbutyl, 1-ethylpropyl, hexyl or 4-methylpentyl. A particular value of (3–6C)cycloalkyl is cyclopropyl, cyclopentyl or cyclohexyl. A particular value for the (1–3C)alkyl portion of (3–6C) cycloalkyl-(1–3C)alkyl, aryl(1–3C)alkyl or heteroaryl (1–3C)alkyl is methylene, ethylene or trimethylene. A particular value for aryl is phenyl, indenyl or naphthyl. A particular value for heteroaryl is furyl, imidazolyl, tetrazolyl, pyridyl (or its N-oxide), thienyl, pyrimidinyl (or its N-oxide), indolyl or quinolinyl (or its N-oxide). A particular value for lower alkyl is methyl, ethyl, propyl, isopropyl, butyl, isobutyl or t-butyl. A particular value for lower acyloxy is acetoxy. A particular value for lower alkoxy is methoxy, ethoxy, propoxy, isoproxy or t-butoxy. A particular value for halogeno is bromo, chloro or fluoro.

A particular value for COORa is carboxy or methoxycarbonyl. A particular value for CONRbRc is carbamoyl or N,N-dimethylcarbamoyl. A particular value for NRgCOR$^2$ is trifluoroacetylamino. A particular value of CONRdSO$_2$R$^1$ is N-phenylsulfonylcarbamoyl or N-(4-chlorophenylsulfonyl)carbamoyl. A particular value for A.X—, taken together, is tris(hydroxymethyl)methylamino, tris(acetoxymethyl)methylamino or 2,2-bis(hydroxymethyl) propoxy.

A particular value for $R^6$ is, for example, isopropyl, cyclopentyl, cyclohexyl, phenyl, furyl, thienyl or pyridyl in which a phenyl or heteroaryl may bear one or two substitutes as defined above.

A more particular value for $R^o$ is isopropyl. A more particular value for J is oxygen. A more particular value for X is a direct bond, imino or oxy. A more particular value for A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for D is methyl, ethyl, isopropyl, tert-butyl, cyclohexyl, phenyl, benzyl, phenethyl, pyridyl, thienyl, 5-tetrazolyl, thiazolyl, quinolinyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for G is methyl, ethyl, benzyl, phenethyl, pyridyl, pyridylmethyl, thenyl, 5-tetrazolylmethyl, or 2-(pyridyl)ethyl, wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

A particular value for R is, for example, hydrogen, trifluoroacetyl, hydroxyoxalyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, sulfo, aminosulfonyl, dimethylaminosulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

A particular value for $Q^1$ and $Q^2$ is, for example, hydroxy, methoxy, ethoxy or isopropoxy; or, when $Q^1$ and $Q^2$ are taken together, a particular value is, for example, the residue derived from 2,3-butanediol, 2,3-dimethyl-2,3-butanediol, 1,3-propanediol, diethanolamine, catechol, (1R,2R,3S,5R)-(−)- or (1S,2S,3R,5S)-(+)-pinanediol, or 2,5-dimethylhexan-3,4-diol. A more particular value for $Q^1$ or $Q^2$ is, for example, methoxy or ethoxy; or, when $Q^1$ and $Q^2$ are taken together, the residue derived from 2,3-dimethylbutane-2,3-diol or 1,3-propanediol.

A particular group of compounds of formula I is one in which $Q^1$, $Q^2$, $R^0$ and R have any of the values defined above and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl, 4-fluorophenyl or 2-thienyl.

Specific compounds of formula I are described in the accompanying Examples. Of these, compounds of particular interest, along with their pharmaceutically acceptable salts, include those described in Examples 2, 15, 19 and 20.

A pharmaceutically acceptable salt of an acidic compound of formula I is one made with a base which affords a pharmaceutically acceptable cation, which includes alkalai metal salts (especially lithium, sodium and potassium), alkaline earth metal salts (especially calcium and magnesium), aluminum salts and ammonium salts, as well as salts made from appropriate organic bases such as triethylamine, morpholine, piperidine and triethanol amine. A pharmaceutically acceptable salt of a basic compound of formula I includes an acid-addition salt made with an acid which provides a pharmaceutically acceptable anion, including #or example, a strong acid such as hydrochloric, sulfuric or phosphoric acid.

It will be noted that other boronic acid derivatives have been disclosed as inhibitors of serine proteases in which the boron substituents corresponding to $Q^1$ and $Q^2$ are acyl, amino or carbamoyl radicals (see, for example, European Patent Application, Publication Number 471 651 A2), and that analogous boronic derivatives corresponding to a compound of formula I are also included as an aspect of the present invention.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Coupling a corresponding acid of formula IIa, or an activated derivative thereof, with a corresponding amine of formula IIb, using a conventional coupling method. An amine of compound IIb conveniently may be used as an acid addition salt and converted into its free base in situ. Conventional coupling methods include coupling with a water soluble carbodimide (Coupling Method A) and the mixed anhydride method (Coupling Method B) as described in Example 1.

(B) For a compound of formula I which contains an N—H residue, removal by using a conventional method of the nitrogen protecting group of a corresponding compound bearing a conventional nitrogen protecting group to afford the compound of formula I which contains an amino N—H residue, particularly for a compound of formula I in which R is hydrogen, removal of a group from a corresponding compound of formula I, or for a compound of formula I in which R has a value of G, the removal of an activating/protecting group Rx from a corresponding compound of formula Vb. Rx is a group which protects and activates a primary amino group for substitution, such as for example benzyloxycarbonyl or trifluoroacetyl. Conventional methods include, for example, removal of a benzyloxycarbonyl group by hydrogenolysis, as described in Example 2; removal of a benzyloxycarbonyl by treatment with a strong acid, for example with trifluoromethanesulfonic acid in an inert solvent such as dichloromethane; and basic hydrolysis of a trifluoroacetyl group.

(C) For a compound of formula I wherein R is an acyl group, acylation of a corresponding amine of formula I wherein R is hydrogen. Convenient methods include, for example, when J is oxygen, the use of an activated carboxylic acid derivative, such as an acid halide, the use of a carboxylic acid and a coupling reagent, the use of an isocyanate for a compound wherein X is imino, and the use of a diactivated carbonic acid derivative, for example, carbonyldiimidazole, phosgene, diphosgene (trichloromethyl chloroformate) or triphosgene (bis (trichloromethyl) carbonate) with an alcohol of formula A.OH, a thiol of formula A.SH or an amine of formula A.NH$_2$ and a base, such as triethylamine or, when J is sulfur, the use of an activated thiocarboxylic acid derivative, such as a thioyl chloride or a lower alkyl ester of a dithioic acid, the use of a thioic acid and a coupling reagent, the use of an isothiocyanate for a compound wherein X is imino, and the use of a diactivated thiocarbonic acid derivative, for example, dimethyl trithiocarbonate, with an alcohol of formula A.OH, a thiol of formula A.SH or an amine of formula A.NH$_2$. In addition, for a compound of formula I in which R is an acyl group of formula A.X.CO— and X is oxy or imino, the acylation may be carried out by converting the corresponding amine of formula I in which R is hydrogen into its corresponding isocyanate, followed by reaction of the isocyanate with an alcohol of formula A.OH or an amine of formula A.NH$_2$, respectively, using a method similar to that described for Example 1, part d.

(D) For a compound of formula I wherein R is a sulfonyl group, sulfonylation of a corresponding amine of formula I wherein R is hydrogen with a corresponding sulfonic acid of formula D.W.SO$_2$.OH, or an activated derivative thereof, such as an acid halide, particularly a sulfonyl (or sulfamoyl) chloride of formula D.W.SO$_2$.Cl. The sulfonylation is conveniently carried out in an inert solvent or diluent, such as dichloromethane, tetrahydrofuran or toluene, at about ambient temperature, using an organic base such as, for example, triethylamine or pyridine, or an inorganic base, such as sodium or potassium carbonate, as an acid acceptor. If a sulfonyl chloride is not commercially available, it may be obtained by a conventional method.

(E) For a compound of formula I in which R is a group G, substitution of the group L of a corresponding compound of formula G-L, wherein L is a conventional leaving group, such as for example halogeno, methylsulfonyloxy, trifluoromethylsulfonyloxy or diazonium, with a corresponding amine of formula I wherein R is hydrogen, optionally using a conventional catalyst.

(F) For a compound of formula I which bears a hydroxy substituent on an aryl or heteroaryl group, cleaving the alkyl ether or acyloxy ester of a corresponding compound of formula I which bears a lower alkoxy or lower acyloxy substituent on an aryl or heteroaryl group. Convenient methods include, for example, the cleavage of a methoxy group using boron tribromide or pyridinium chloride and the cleavage of a t-butoxy group using trifluoroacetic acid for an alkyl ether, and the acidic or alkaline hydrolysis of an acyloxy group.

(G) For a compound of formula I which bears a group of formula COORa in which Ra is hydrogen (a carboxy group), decomposing the ester group of a corresponding ester made with a conveniently removed acid protecting group, for example a corresponding compound of formula I in which Ra is not hydrogen. The decomposition may be carried out using any one of the variety of procedures well known in organic chemistry, for example basic hydrolysis using lithium or sodium hydroxide, or by hydrogenolysis of a benzyl ester.

(H) For a compound of formula I bearing a moiety of formula COORa, CH$_2$COORa, CONRbRc CH$_2$CONRbRc, COO(CH$_2$)$_2$NReRf or CONRdSO$_2$R$^1$, acylation of a corresponding compound of formula HORa, HNRbRc, HO(CH2)$_2$NReRf or HNRdSO$_2$R$^1$ with a corresponding acid of formula I bearing a moiety of formula COORa in which Ra is hydrogen, or an activated derivative thereof.

(I) For a compound of formula I bearing a lower acyloxy group or a group of formula NRgCHO, NRgCOR$^2$, NRgCOOR$^2$, NRhCQNRiRj or NRkSO$_2$R$^3$, acylation or sulfonylation of a corresponding compound of formula I bearing a hydroxy group or an amino group of formula NHRg, NHRh or NHRk (i.e. an amino group of formula NReRf is which Re is hydrogen and Rf is Rg, Rh or Rk) with an activated derivative of a corresponding acid of formula HOCHO, HOCOR$^2$, HOCOOR$^2$, HOCQNRiRj (including an isocyanate or isothiocyanate) or HOSO$_2$R$^3$ respectively, using a conventional method.

(J) For a compound of formula I which bears a heteroaryl N-oxide group, oxidation of a corresponding compound of formula I which bears a heteroaryl group using a conventional oxidant, such as for example dioxirane in acetone.

(K) For a compound of formula I which bears a primary amino group, reduction of a corresponding compound bearing a nitro group using a conventional reducing method, such as for example, hydrogenation over a palladium catalyst, or reduction with tin(II) chloride.

(L) For a compound of formula I in which Q$^1$ and/or Q$^2$ is hydroxy, conversion of the corresponding group Q$^1$ and/or Q$^2$ of a compound of formula I in which Q$^1$ and/or Q$^2$ is not hydroxy into a hydroxy group by a conventional method. Conventional method include, for example, hydrogenolysis of a group in which Q$^1$ and/or Q$^2$ is benzyl or hydrolysis of a group Q$^1$ and/or Q$^2$ with aqueous acid.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples. For uniformity and clarity, compounds herein are represented as the 6-pyrimidone, rather than the 6-hydroxypyrimidine, tautomers.

As will be clear to one skilled in the art, a variety of sequences is available for preparation of the starting materials. According to one of the available routes, a key intermediate pyrimidin-6-one-1-acetic acid of formula III may be prepared as shown in Scheme I (set out, together with other Schemes, following Examples) and as described in the Examples. In the Schemes, CBZ represents a benzyloxycarbonyl group.

In general, a nitrile of formula R$^6$CN is converted into a corresponding imidic ester of formula IV wherein R$^7$ is methyl or ethyl, conveniently isolated as its hydrochloride, if the imidic ester is not commercially available. Reaction of the imidic ester with an amine of formula H$_2$NCH$_2$R$^8$ in which R$^8$ is a latent or protected carboxaldehyde group, such as vinyl, dimethoxymethyl or diethoxymethyl, affords a corresponding amidine of formula V, conveniently isolated as its hydrochloride salt. Cyclization of an amidine of formula V with diethyl ethoxymethylenemalonate affords a corresponding ethyl 1,2-disubstituted-6-pyrimidone-5-carboxylate of formula VI which is hydrolyzed to the 1,2-disubstituted-6-pyrimidone-5-carboxylic acid of formula VII.

An acid of formula VII may be converted into a corresponding isocyanate of formula VIII by a conventional method, for example by using diphenylphosphoryl azide in an inert solvent, as described in the examples. Conveniently, the isocyanate is not isolated, but is converted into a benzyl urethane of formula IX as also is shown in Scheme I. It will be clear to one skilled in the art that, in general, treatment of an isocyanate of formula VIII with a selected alcohol or amine of formula A.X.H in which X is oxy or imino will provide a corresponding product of formula IXa in which X is oxy or imino, and that the product of formula IXa may be carried forward to a corresponding product of formula I using one of the routes outlined below.

Transformation of R$^8$ into a carboxaldehyde to afford a corresponding compound of formula X from a compound of formula IX is the next step. If $R^8$ is a vinyl group, the transformation may be carried out using N-methylmorpholine-N-oxide and osmium tetroxide, as described in Example 1, part e. If $R^8$ is a dimethoxymethyl or diethoxyethyl group, the acetal may be hydrolyzed with dilute hydrochloric acid, as described in Example 3, part f. Oxidation of an acetaldehyde derivative of formula X to provide a corresponding substituted acetic acid of formula III is conveniently carried out as described in Example 1, part f, using sodium chlorite as the oxidant. It will be noted that an acid of formula III is an acid of formula IIa in which R is benzyloxycarbonyl.

Coupling an acid of formula III with an amine of formula IIb, as described in process (A) above, affords a corresponding compound of formula I wherein R is benzyloxycarbonyl. Removal of the nitrogen protecting group of a compound of formula I wherein R is benzyloxycarbonyl by hydrogenolysis, for example as described in Example 2, affords a corresponding amine of formula I wherein R is hydrogen. (See Scheme II.)

A preferred method for introducing the substituent R when it is a group G, particularly when it is an alkyl or substituted alkyl group, is by the use of a corresponding compound in which the pyrimidone 3-amino substituent bears an activating/protecting group of formula Rx, for example, benzyloxycarbonyl or trifluoroacetyl. Thus, acylation of a compound of formula I wherein R is hydrogen with trifluoroacetic anhydride affords a corresponding compound of formula Va in which Rx is trifluoroacetyl. It will be noted that a compound of formula Va in which Rx is benzyloxycarbonyl or trifluoroacetyl is also a compound of formula I in which R is an acyl group. Alkylation, using a corresponding reagent of formula G.L in which G is alkyl or substituted alkyl, then provides a corresponding intermediate of formula Vb.

The preparation of intermediate amines of formula IIb is well known in the art. The preparation of compounds of formula IIb in which $Q^1$ and $Q^2$ together form the residue of a dihydroxy compound is particularly described in U.S. Pat. No. 4,537,773 of 27 Aug. 1985.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

Inhibition Measurements

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. No. 4,910,190. In general, the $K_i$ values for Compounds of the invention which were tested are generally on the order of $10^{-7}$M or much less.

Acute Lung Injury Model

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model (described in Williams et al., *American Review of Respiratory Disease* (1991), 144, 875–883) was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 µg), or by dosing them intravenously or orally as solutions at various times prior to the HLE challenge (100 µg) to determine their utility in preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid) may be added as indicated to achieve solution. Compounds of this invention produced statistically significant reductions in wet lung weight and total lavagable cells relative to HLE alone.

Acute Hemorrhagic Assay

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respiratory Disease* (1990), 141, 672–677, is as follows. Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 µg/animal of HNE in 300 µL phosphate buffered saline (PBS) pH 7.4. Four hours after enzyme administration, the animals are killed with an overdose of pentobarbital sodium, the thorax opened and the lungs and trachea removed. The excised lungs are lavaged with three changes of 2 mL normal saline via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The (μL blood equivalents)/(mL lavage) are determined by comparing the OD of the test samples with the OD of the standard curve prepared from whole hamster blood. The total μL equivalents of blood recovered is determined by multiplying recovered lavage volume by the (μL blood equivalents)/(mL lavage) for each sample. Results are reported as % inhibition of hemorrhage with respect to PBS treated controls when the test compound is given at a specified dose and time prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. As noted above, a compound of formula I in which $O^1$ and/or $Q^2$ is not hydroxy may be converted into a corresponding compound of formula $Q^1$ and/or $Q^2$ is hydroxy under the condition of an in vivo or in vitro test. Accordingly, in general the in vitro inhibition measurements were done at intervals, such as overnight, which ensured complete hydrolysis of the boronate esters. It should be noted that, as would be expected in comparison of in vitro and in vivo results, there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorragic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In a liquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, a 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of the HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route, either alone or simultaneously or sequentially with other therapeutically active agents customarily administered for the condition.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); if "acidic silica gel" is indicated, material custom prepared by J. T. Baker Chemical Co., Phillipsburg, N.J., USA, and having a pH of about 6 when slurried in water was used; reversed phase chromatography means flash chromatography over octadecylsilane (ODS) coated support having a particle diameter of 32–74μ, know as "PREP-40-ODS" (Art 731740-100 from Bodman Chemicals, Aston, Pa., USA); thin layer chromatography (TLC) was carried out on 0.25 mm silica gel GHLF plates (Art 21521 from Analtech, Newark, Del., USA); reversed phase-TLC (RP-TLC) was carried out Whatman MKC$_{18}$F plates (Art 4803-110 from Bodman Chemicals);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-d$_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported.

EXAMPLE 1

2-(5-Benzyloxycarbonylamino-6-oxo-2-phenyl-1,6-dihydro-1-pyrimidinyl)-N-[2-methyl-1-(4,4,5,5-tetramethyl-1,3,2-dioxaborolidin-2-yl)propyl] acetamide A solution of 5-benzyloxycarbonylamino-6-oxo-2-phenyl-1,6-dihydro-1-pyrimidinylacetic acid (2.0 g) and 4-methylmorpholine (0.60 mL) in tetrahydrofuran (30 mL) was cooled to −25° C. The dropwise addition of isobutyl chloroformate (0.19 mL), over 4 minutes, caused formation of a white precipitate. The mixture was stirred at a bath temperature of −30° to −25° C. for 30 minutes and 4-methylmorpholine (0.16 mL) and 2-methyl-1-(4,4,5,5-tetramethyl-1,3,2-dioxaborolidin-2-yl)propylammonium trifluoroacetate (0.43 g) were added. Stirring was continued at −25° C. for 15 minutes, before allowing the mixture to warm to room temperature overnight. The white precipitate was removed by filtration through a medium fritted glass funnel and the filtrate was concentrated to a pink foam. Chromatography, with methanol:chloroform (2:98) as the eluent, gave the title compound (2.56 g), as a white solid; TLC: R$_f$=0.30, methanol:chloroform (2:98); 300 MHz NMR: 0.83 (d,3, J=6.7), 0.84 (d,3, J=6.7), 1.17 (s,12), 1.70–1.81 (m,1), 2.67 (t,1, J=5), 4.47 (s,2), 5.19 (s,2), 7.34–7.55 (m,10), 8.27 (d,1, J=5), 8.46 (s,1), 8.96 (s,1); MS: m/z=561(M+1). Analysis for C$_{30}$H$_{37}$BN$_4$O$_6$: Calculated: C, 64.29; H, 6.65; N, 10.00; Found: C, 64.09; H, 6.71; N, 9.80.

The intermediate 5-benzyloxycarbonylamino-6-oxo-2-phenyl-1,6-dihydro-1-pyrimidinylacetic acid was prepared as follows:

a. N-Allylbenzamidine hydrochloride. To a solution of ethyl benzimidate hydrochloride (20 g) in methanol at 0° C. was added allyl amine. The resulting solution was allowed to stand for 2 days at 5° C. The solution was evaporated to yield a solid which was collected and washed with ether to give N-allylbenzamidine hydrochloride (21.5 g) as a white solid; 300 MHz NMR: 10.1 (s,1), 9.68 (s,1), 9.29 (s,1), 7.72 (s,5), 5.92 (m,1), 5.35 (d,2), 5.26 (d,2), 4.14 (s,2).

b. Ethyl 1-allyl-2-phenylpyrimidin-6(1H)-one-5-carboxylate. The free base of N-allylbenzamidine hydrochloride was generated by dissolving N-allylbenzamidine hydrochloride (79.7 g) in 1N sodium hydroxide. The free base was then extracted into dichloromethane, which was dried and evaporated to provide N-allylbenzamidine (65.2 g). This was added to diethyl ethoxymethylenemalonate (78 mL) in ethanol (50 mL). The resulting solution was heated at 120° C. for 2 hours. The solution was cooled, diluted with ethyl acetate, washed (saturated ammonium chloride, water), dried, and evaporated to give a solid, which was collected and washed two times with ether:hexane (1:1), to provide ethyl 1-allyl-2-phenylpyrimidin-6(1H)-one-5-carboxylate (62.5 g) as a white solid; 300 MHz NMR: 8.56 (s,1), 7.54 (m,5), 5.80 (m,1), 5.09 (d,1), 4.82 (d,1), 4.47 (d,2), 4.28 (q,2), 1.28 (t,3).

c. 1-Allyl-2-phenylpyrimidin-6(1H)-one-5-carboxylic acid. To a solution of ethyl 1-allyl-2-phenylpyrimidin-6(1H)-one-5-carboxylate (25.6 g) in tetrahydrofuran (300 mL) at 0° C. was added a solution of 0.5N sodium hydroxide (198 mL). The resulting solution was allowed to stir for 1 hour, was poured into dichloromethane and the organic layer removed. The remaining aqueous fraction was extracted with dichloromethane, acidified with 1N hydrochloric acid (pH 2), and extracted with dichloromethane. The organic extracts from the acidified extraction were dried and evaporated to give an oil which crystallized upon addition of ether. The resulting white solid was collected and washed with ether:hexane (1:1) to give 1-allyl-2-phenylpyrimidin-6(1H)-one-5-carboxylic acid (11.1 g); 300 MHz NMR: 13.0 (s broad,1), 8.69 (s,1), 7.58 (m,5), 5.82 (m,1), 5.16 (d,1), 4.87 (d,1), 4.51 (d,2).

d. 1-Allyl-5-benzyloxycarbonylamino-2-phenylpyrimid-6(1H)-one. To a solution of 1-allyl-2-phenylpyrimidin-6 (1H)-one-5-carboxylic acid (30.2 g), and triethylamine (32.8 mL) in dioxane (390 mL) was added diphenylphosphoryl azide (25.6 mL) and the resulting solution was heated at 100° C. for 2 hours. Benzyl alcohol (24.5 mL) was added and the resulting solution heated at 100° C. for 12 hours. The solution was cooled and the solvent evaporated. The residue was dissolved in ethyl acetate, washed (saturated ammonium chloride, 1N sodium hydroxide, water), dried, and evaporated to give an oil, which crystallized upon addition of ether to give a white solid that was collected and washed with ether to provide 1-allyl-5-benzyloxycarbonylamino-2-phenylpyrimid-6(1H)-one (25.1 g); 300 MHz NMR: 8.93 (s,1), 8.45 (s,1), 7.43 (m,10), 5.75 (m,1), 5.18 (s,2), 5.08 (d,1), 4.82 (d,1), 4.46 (d,2).

e. 5-Benzyloxycarbonylamino-6-oxo-2-phenyl-1,6-dihydro-1-pyrimidinylacetaldehyde. To a solution of 1-allyl-5-benzyloxycarbonylamino-2-phenyl-pyrimid-6(1H)-one in tetrahydrofuran (200 mL) and water (30 mL) was added 4-methylmorpholine oxide (9.82 g) and osmium tetroxide (4.4 mL, 4% in water). The resulting solution was allowed to stir overnight. 4-Methylmorpholine oxide (1.65 g) was added and the solution was allowed to stir for 4 hours. Sodium thiosulfate (saturated aqueous solution, 10 mL) and diatomoaceous earth (30 g) were added and the mixture was stirred for 0.5 hour. The mixture was filtered and evaporated to give an oil. This oil was dissolved in ethyl acetate, washed (saturated aqueous sodium thiosulfate solution, 1N hydrochloric acid, brine), and evaporated to give an oil. The oil was dissolved in ethanol (230 mL) and a solution of sodium periodate (27 g) in water (40 mL) was added. The mixture was stirred for 2 hours, filtered through diatomaceous earth and evaporated. The residue was dissolved in ethyl acetate, washed with water, dried, and evaporated to provide 5-benzyloxcarbonylamino-6-oxo-2-phenyl-1,6-dihydro-1-pyrimidinylacetaldehyde (25 g) as a white solid; TLC: $R_f$=0.8, ethyl acetate:diethyl ether (1:1).

f. 5-Benzyloxycarbonylamino-6-oxo-2-phenyl-1,6-dihydro-1-pyrimidinylacetic acid. To a solution of 5-benzyloxycarbonylamino-6-oxo-2-phenyl-1,6-dihydro-1-pyrimidinylacetaldehyde (25 g) in tert-butyl alcohol (175 mL), and 2-methyl-2-butene (148 mL) at 0° C. was added a solution of sodium chlorite (57 g) and sodium dihydrogen phosphate monohydrate (67 g) in water (190 mL). The mixture was allowed to stir for 3 hours and was evaporated. The resulting material was diluted with ethyl acetate and extracted with 1N aqueous sodium hydroxide. The aqueous solution was acidified to pH 3 with hydrochloric acid and was extracted with dichloromethane. The organic extracts were dried and evaporated to give a white solid, which was washed with ether:hexane (1:1) to yield the acid (17.2 g); 300 MHz NMR: 13.3 (s,1), 9.04 (s,1), 8.48 (s,1), 7.43 (m,10), 5.19 (s,2), 4.51 (s,2).

The intermediate 2-methyl-1-(4,4,5,5-tetramethyl-1,3,2-dioxaborolidin-2-yl)propylammonium trifluoroacetate was prepared using the procedures in Examples 1.g.–1.j. below, which are similar to those described in *J. Biol. Chem.* (1984), 259, 15106–15114.

g. 2-Isopropyl-4,4,5,5-tetramethyl-1,3,2-dioxaborolidine. A dry, 5 L, three-necked flask was equipped with a mechanical stirrer, a Claisen adapter holding a low-temperature thermometer and an addition funnel, and a second Claisen adapter holding an addition funnel and a nitrogen inlet. Isopropylmagnesium chloride (1.60 L, 2.0M in tetrahydrofuran) was transferred via cannula into one addition funnel, and triethylborate (467.1 g) was placed into the other addition funnel. Tetrahydrofuran (1 L) was placed in the reaction flask and was cooled to –78° C. The triethylborate and the Grignard reagent were simultaneously added dropwise over a 2 hour period, while maintaining an internal temperature of less than –50° C. Upon completion of the addition, the mixture was stirred for an additional 2 hours at –78° C. The reaction was quenched by dropwise addition of concentrated hydrochloric acid (600 mL) over 1 hour. The temperature of the mixture rose from –78° C. to –20° C., and the dark amber solution became colorless. The mixture was stirred overnight, evaporated, and extracted with ether. The combined extracts were washed with brine and dried (MgSO$_4$). Evaporation gave crude (dihydroxy)isopropylborane as a white semi-solid (360.2 g). This material was dissolved in ethyl acetate (1 mL) and the solution was placed in a 3 L, 3-necked flask equipped with a mechanical stirrer and a nitrogen inlet. To the solution was added 2,3-dimethyl-2,3-butanediol (378 g) and anhydrous magnesium sulfate (200 g). The mixture was allowed to stir for 70 hours, the solids were removed by filtration, and the filtrate was evaporated to yield an amber oil. The oil was purified by two fractional distillations at reduced pressure. The fraction (184.9 g) which initially distilled at 60°–97° C. (6000 Pa) was redistilled to yield the dioxoborolidine (164.0 g) as a pale yellow oil; bp 74°–78° C. (6500 Pa); 300 MHz NMR: 0.87–0.94 (m,7), 1.17 (s,12); MS: m/z=171(M+1).

h. 2-(1-Chloro-2-methylpropyl)-4,4,5,5-tetramethyl-1,3,2-dioxaborolidine. A dry, 3 L, three-necked flask was equipped with a mechanical stirrer, a condenser capped with a nitrogen inlet and a Claisen adapter holding a low-temperature thermometer and an addition funnel. Dichloromethane (92.8 g) and tetrahydrofuran (600 mL) were added to the flask and cooled to –78° C. n-Butyllithium solution (421 mL, 2.5M in hexanes) was transferred via cannula into the addition funnel. The n-butyllithium was added dropwise over 3 hours while maintaining the internal temperature at –78° C. The reddish-brown solution was treated with the product from Example 1.g. (128.0 g) by dropwise addition over 10 minutes. The reaction mixture was stirred for 1 hour while warming slowly to –40° C. The mixture was cooled to –78° C. and a zinc chloride solution (490 mL, 1.0M in ether) was added over 15 minutes. The mixture was stirred for 15 minutes at –78° C. and allowed to warm to room temperature overnight. The mixture was evaporated, dissolved in ether, washed (saturated ammonium chloride, water), dried (MgSO$_4$) and evaporated to give a brown oil (149.2 g). Fractional distillation under reduced pressure gave the chloride (123.5 g) as a pale yellow oil; bp 105°–122° C. (2700 Pa); NMR: 0.92–0.97 (m,6), 1.15–1.23 (m,12), 1.98 (m,1), 3.32 (d,1); MS: m/z=219(M+1).

i. 2-[1-[N,N-Bis(trimethylsilyl)amino]-2-methylpropyl]-4,4,5,5-tetramethyl-1,3,2-dioxaborolidine. A 2 L, 3-necked flask was equipped with a mechanical stirrer, an addition funnel and a Claisen adapter holding a low-temperature thermometer and a nitrogen inlet. The flask was charged with a tetrahydrofuran (800 mL) solution of 1,1,1,3,3,3-hexamethyldisilazane (120.8 g), and the addition funnel was charged with n-butyllithium solution (300 mL, 2.5M in hexane). The n-butyllithium was added dropwise to the cooled reaction vessel over 30 minutes. The internal temperature was maintained in the range –78° to –60° C. during the course of the addition. The reaction mixture was warmed to 0° C. for 30 minutes, was cooled to –78° C., and the product from Example 1.h. (163.5 g) was added dropwise over 15 minutes. When the addition was complete, the cooling bath was removed and the mixture was allowed to warm to room temperature overnight. The orange suspension was filtered to remove solids and the filtrate was evaporated. The residue was filtered to remove solids and the filter cake was washed with ether. Concentration of the filtrate gave an oil which was fractionally distilled at reduced pressure to give the amine (212.8 g) as a colorless oil; bp 96°–106° C. (200 Pa); NMR: 0.11 (s,18), 0.86 (m,7), 1.19 (m,12), 1.75 (m,1); MS: m/z=344(M+1).

j. 2-Methyl-1-(4,4,5,5-tetramethyl-1,3,2-dioxaborolidin-2-yl)propylammonium trifluoroacetate. A 2 L, 3-necked flask was equipped with a mechanical stirrer, a condenser capped with a nitrogen inlet and a Claisen adapter holding a thermometer and an addition funnel. The vessel was charged with a hexane (1 L) solution of the product from Example 1.i., the solution was cooled to 3° C. (ice/water bath) and trifluoroacetic acid (226.5 g) was added over 10 minutes. The temperature of the mixture rose to 25° C. over the course of the addition and a white precipitate formed. The mixture was stirred for 1 hour at 5° C., filtered, and the white solid was collected, washed with hexane, and dried, to afford the ammonium salt (116.8 g) as a white powder; mp 131°–133° C.; 300 MHz NMR: 0.95 (t,6), 1.25 (s,12, 1.92–1.97 (m,1), 2.62 (broad s, 1)7.80 (broad s, 2); MS: m/z=200(M+1).

EXAMPLE 2

2-(5-Amino-6-oxo-2-phenyl-1,6-dihydro-1-pyrimidinyl)-N-[2-methyl-1-(4,4,5,5-tetramethyl-1,3,2-dioxaborolidin-2-yl)propyl]acetamide To a solution of the product from Example 1 (2.55 g) in tetrahydrofuran (50 mL) was added 10% (w/w) palladium on carbon (0.53 g) and the suspension was stirred under hydrogen overnight. The mixture was filtered through diatomaceous earth and evaporated to give a pale grey foam (2.10 g). A portion (0.41 g) of this material was purified by chromatography, with methanol:chloroform (3:97) as the eluent, to give the title compound (0.19 g) as a white solid; TLC: $R_f$=0.33, methanol:chloroform (2:98); 300 MHz NMR: 0.84 (d,3, J=6.7), 0.85 (d,3, J=6.7), 1.67–1.84 (m,1), 2.59 (t,1, J=6), 4.43 (s,2), 5.17 (s,2), 7.32 (s,1), 7.41–7.49 (m,5), 8.31 (d,1, J=5); MS: m/z=427(M+1). Analysis for $C_{22}H_{31}BN_4O_4 \cdot 0.7 H_2O$: Calculated: C, 60.20; H, 7.44; N, 12.76; Found: C, 60.44; H, 7.24; N, 12.30.

EXAMPLE 3

2-[5-Benzyloxycarbonylamino-6-oxo-2-(4-fluorophenyl)-1,6-dihydro-1-pyrimidinyl]-N-[2-methyl-1-(4,4,5,5-tetramethyl-1,3,2-dioxaborolidin-2-yl)propyl]acetamide.

5-Benzyloxycarbonylamimo-2-(4-fluorophenyl)-6-oxo-1,6-dihydo-1-pyrimidinylacetic acid and 2-methyl-1-(4,4,5,5-tetramethyl-1,3,2-dioxaborolidin-2-yl)propylammonium trifluoroacetate were coupled using a procedure similar to that described in Example 1 to yield material which was purified by chromatography, with tetrahydrofuran:dichloromethane (gradient, 4:96, 10:90) as the eluent, to give the title compound as a white solid; NMR: 8.98 (s,1), 8.44 (s,1), 8.26 (d,1), 7.60 (q,2), 7.35 (m,7), 5.18 (s,2), 4.49 (s,2), 2.69 (t,1), 1.72 (m,1), 1.16 (s,12), 0.82 (d,6); MS: m/z=579(M+1). Analysis for $C_{30}H_{36}BFN_4O_6$: Calculated: C, 62.3; H, 6.27; N, 9.68; Found: C, 62.2; H, 6.36; N, 9.65.

The intermediate 5-benzyloxycarbonylamimo-2-(4-fluorophenyl)-6-oxo-1,6-dihydo-1-pyrimidinylacetic acid was prepared as follows:

a. Ethyl 4-fluorobenzimidate hydrochloride. A solution of 4-fluorobenzonitrile (50 g) in tetrahydrofuran (300 mL) and ethanol (60.5 mL) at 0° C. was saturated with anhydrous hydrogen chloride gas and the resulting solution was allowed to stand overnight. The solvent was evaporated and the resulting solid was collected and washed with ether to provide ethyl 4-fluorobenzimidate hydrochloride (20 g) as a white solid; NMR: 8.27 (m,2), 7.51 (m,2), 4.63 (q,2), 1.47 (t,3).

b. N-(2,2-Diethoxyethyl)-4-fluorobenzamidine. To a solution of ethyl 4-fluorobenzimidate hydrochloride (18.5 g) in ethanol (90 mL) at 0° C. was added aminoacetaldehyde diethyl acetal (14.5 mL) and the resulting solution was kept at 5° C. overnight. The solvent was evaporated, the resulting oil dissolved in 1N NaOH (200 mL), and the solution extracted several times with dichloromethane. The organic extracts were dried and evaporated to provide N-(2,2-diethoxyethyl)-4-fluorobenzamidine (21 g) as an oil; MS: m/z=255(M+1).

c. Ethyl 1-(2,2-diethoxyethyl)-2-(4-fluorophenyl) pyrimid-6(1H)-one-5-carboxylate. Diethyl ethoxymethylenemalonate and N-(2,2-diethoxyethyl)-4-fluorobenzamidine were subjected to a procedure similar to that described in Example 1.b. to obtain ethyl-1-(2,2-diethoxyethyl)-2-(4-fluorophenyl)pyrimin-6(1H)-one-5-carboxylate as an oil; MS: m/z=379(M+1).

d. 1-(2,2-Diethoxyethyl)-2-(4-fluorophenyl)pyrimidin-6(1H)-one-5-carboxylic acid. Ethyl 1-(2,2-diethoxyethyl)-2-(4-fluorophenyl)pyrimidin-6(1H)-one-5-carboxylate was subjected to a procedure similar to that described in Example 1.c. to give the acid as a white solid; 300 MHz NMR: 8.66 (s,1), 7.69 (m,2), 7.40 (m,2), 4.69 (t,1), 4.05 (d,2), 3.39 (m,4), 0.99 (t,6).

e. 5-Benzyloxycarbonylamino-6-oxo-2-(4-fluorophenyl)-1,6-dihydro-1-pyrimidinylacetaldehyde diethyl acetal. 1-(2,2-Diethoxyethyl)-2-(4-fluorophenyl)pyrimidin-6(1H)-one-5-carboxylic acid was subjected to a procedure similar to that described in Example 1.d. to give the diethyl acetal as a white solid; TLC: $R_f$=0.6, ether:hexane (3:1).

f. 5-Benzyloxycarbonylamino-6-oxo-2-(4-fluorophenyl)-1,6-dihydro-1-pyrimidinylacetaldehyde. A solution of 5-benzyloxycarbonylamino-6-oxo-2-(4-fluoro-phenyl)-1,6-dihydro-1-pyrimidinylacetaldehyde diethyl acetal in tetrahydrofuran (7 mL) and 1N hydrochloric acid (5 mL) was heated at 60° C. for 18 hours. The solution was cooled and neutralized with saturated sodium bicarbonate solution to pH 6. The solution was extracted with ethyl acetate and the organic extracts dried and evaporated to give 5-benzyloxycarbonylamino-6-oxo-2-(4-fluorophenyl)-1,6-dihydro-1-pyrimidinylacetaldehyde as a white solid; NMR: 9.51 (s,1), 9.03 (s,1), 8.47 (s,1), 7.43 (m,9), 5.19 (s,2), 4.76 (s,2).

g. 5-Benzyloxycarbonylamino-6-oxo-2-(4-fluorophenyl)-1,6-dihydro-1-pyrimidinylacetic acid. 5-Benzyloxycarbonylamino-6-oxo-2-(4-fluorophenyl)-1,6-dihydro-1-pyrimidinylacetaldehyde was subjected to a procedure similar to that described in Example 1.f. to provide 5-benzyloxycarbonylamino-6-oxo-2-(4-fluorophenyl)-1,6-dihydro-1-pyrimidinylacetic acid as a white solid; 300 MHz NMR: 9.06 (s,1), 8.46 (s,1), 7.42 (m,9), 5.19 (s,2), 4.52 (s,2).

EXAMPLES 4–7

The following compounds of formula I wherein $Q^1$ and $Q^2$ together with the boron to which they are attached form a 4,4,5,5-tetramethyl-1,3,2-dioxaborolidin-2-yl group, R is benzyloxycarbonyl, $R^0$ is isopropyl and $R^6$ is the indicated group were prepared using a coupling procedure similar to that described in Example 3.

EXAMPLE 4

$R^6$=4-chlorophenyl

Purified by chromatography, with dichloromethane:tetrahydrofuran (gradient, 95:5, 90:10) as the eluent; 300 MHz NMR: 8.97 (s,1), 8.45 (s,1), 8.25 (d,1), 7.55 (m,4), 7.40 (m,5), 5.19 (s,2), 4.49 (s,2), 2.69 (t,1), 1.75 (m,1), 1.16 (s,12), 0.83 (d,6); MS: m/z=595(M+1). Analysis for $C_{30}H_{36}BClN_4O_6$: Calculated: C, 60.61 H, 6.10; N, 9.42; Found: C, 60.4; H, 6.09; N, 9.34.

EXAMPLE 5

$R^6$=4-methoxyphenyl

Purified by chromatography, with dichloromethane:tetrahydrofuran (gradient, 95:5, 90:10) as the eluent; NMR: 8.90 (s,1), 8.43 (s,1), 8.30 (d,1), 7.45 (m,7), 6.98 (d,2), 5.18 (s,2), 4.50 (s,2), 3.81 (s,3), 2.68 (t,1), 1.77 (m,1), 1.19 (broad s,12), 0.85 (d,6); MS: m/z=591(M+1). Analysis for $C_{31}H_{39}BN_4O_7$: Calculated: C, 63.1; H, 6.65; N, 9.49; Found: C, 63.3; H, 6.63; N, 9.10.

EXAMPLE 6

$R^6$=2-thienyl

Purified by chromatography, with dichloromethane:tetrahydrofuran (gradient, 95:5, 90:10) as the eluent; NMR: 8.96 (s,1), 8.48 (d,1), 8.43 (s,1), 7.84 (d,1), 7.39 (m,6), 7.14 (t,1), 5.18 (s,2), 4.78 (s,2), 2.68 (t,1), 1.81 (m,1), 1.16 (broad s,12), 0.89 (d,6); MS: m/z=567(M+1). Analysis for $C_{28}H_{35}BN_4O_6S$: Calculated: C, 59.4; H, 6.23; N, 9.89; Found: C, 59.5; H, 6.26; N, 9.05.

EXAMPLE 7

$R^6$=isopropyl

Purified by chromatography, with dichloromethane:tetrahydrofuran (gradient, 96:4, 90:10) as the eluent; NMR: 8.75 (s,1), 8.55 (d,1), 8.30 (s,1), 7.40 (m,5), 5.16 (s,2), 4.84 (s,2), 2.93 (m,1), 2.68 (t,1), 1.79 (m,1), 1.19 (d,6), 1.14 (broad s,12), 0.89 (d,6); MS: m/z=527(M+1). Analysis for $C_{27}H_{39}BN_4O_6$: Calculated: C, 61.6; H, 7.47; N, 10.6; Found: C, 61.6; H, 7.43; N, 10.4.

The pyrimidone acetic acids possessing the required $R^6$ substituent for the coupling reactions described in Examples 4–7, were prepared using procedures similar to those outlined in Example 3.a.–Example 3.g. by replacing 4-fluorobenzonitrile with the required nitrile in the step corresponding to Example 3.a.

EXAMPLES 8–12

The following compounds of formula I wherein $Q^1$ and $Q^2$ together with the boron to which they are attached form a 4,4,5,5-tetramethyl-1,3,2-dioxaborolidin-2-yl group, R is hydrogen, $R^0$ is isopropyl, and $R^6$ is the indicated group were prepared from the corresponding benzyloxycarbonylamino compounds, from Examples 3–7, using a hydrogenolysis procedure similar to that described in Example 2.

EXAMPLE 8

$R^6$=4-fluorophenyl

Purified by chromatography, with dichloromethane:methanol (gradient, 96:4, 94:6) as the eluent; 300 MHz NMR: 8.29 (d,1), 7.53 (m,2), 7.31 (s,1), 7.23 (t,2), 5.19 (s,2), 4.45 (s,2), 2.62 (t,1), 1.70 (m,1), 1.16 (broad s,12), 0.82 (d,3), 0.85 (d,3); MS: m/z=445(M+1). Analysis for $C_{22}H_{30}BFN_4O_4$: Calculated: C, 59.5; H, 6.80; N, 12.6; Found: C, 59.4; H, 6.81; N, 12.4.

EXAMPLE 9

$R^6$=4-chlorophenyl

Purified by chromatography, with dichloromethane:tetrahydrofuran (gradient, 85:15, 60:40) as the eluent; 300 MHz NMR: 8.29(d,1), 7.48 (m,4), 7.32 (s,1), 5.22 (d,2), 4.46 (s,2), 2.64 (m,1), 1.76 (m,1), 1.17 (broad s,12), 0.84 (d,6); MS: m/z=461(M+1). Analysis for $C_{22}H_{30}BClN_4O_4$: Calculated: C, 57.4; H, 6.56; N, 12.2; Found: C, 58.0; H, 6.58; N, 12.1.

EXAMPLE 10

$R^6$=4-methoxyphenyl

Purified by chromatography, with dichloromethane:methanol (gradient, 96:4, 90:10) as the eluent; NMR: 8.33 (d,1), 7.42 (d,2), 7.30 (s,1), 6.92 (d,2), 5.11 (s,2), 4.45 (s,2), 3.79 (s,3), 2.60 (t,1), 1.75 (m,1), 1.16 (broad s,12), 0.85 (m,6); MS: m/z=457(M+1). Analysis for $C_{23}H_{33}BN_4O_5 \cdot 0.15 H_2O$: Calculated: C, 60.2; H, 7.31; N, 12.2; Found: C, 60.4; H, 7.48; N, 11.8.

EXAMPLE 11

$R^6$=2-thienyl

Purified by chromatography, with dichloromethane:tetrahydrofuran (gradient, 85:15, 60:40) as the eluent; NMR: 8.49 (d,1), 7.69 (d,1), 7.31 (s,2), 7.08 (t,1), 5.30 (s,2), 4.73 (s,2), 2.64 (t,1), 1.80 (m,1), 1.18 (broad s,12), 0.89 (m,6); MS: m/z=433(M+1). Analysis for $C_{20}H_{29}BN_4O_4S \cdot 0.25 H_2O$: Calculated: C, 55.0; H, 6.81; N, 12.8; Found: C, 54.8; H, 6.81; N, 12.8.

EXAMPLE 12

$R^6$=isopropyl

Purified by chromatography, with dichloromethane:tetrahydrofuran (gradient, 85:15, 60:40) as the eluent; NMR: 8.57 (d,1), 7.21 (s,1), 4.81 (d,4), 2.82 (m,1), 2.58 (t,1), 1.77 (m,1), 1.11 (s broad,18), 0.88 (m,6); MS: m/z=393(M+1). Analysis for $C_{19}H_{33}BN_4O_4$: Calculated: C, 58.2; H, 8.48; N, 14.3; Found: C, 58.1; H, 8.34; N, 14.2.

EXAMPLE 13

2-(5-Acetylamino-6-oxo-2-phenyl-1,6-dihydro-1-pyrimidinyl)-N-[2-methyl-1-(4,4,5,5-tetramethyl-1,3,2-dioxaborolidin-2-yl)propyl]acetamide.

To a solution of the product from Example 2 (0.30 g) in dichloromethane (7 mL) was added triethylamine (0.11 mL) and acetyl chloride (55 uL). The reaction mixture was stirred overnight at room temperature. Evaporation gave a green-grey foam which was purified by chromatography, with chloroform:methanol (gradient, 50:1, 30:1) as the eluent, to yield the title compound (0.19 g) as a white powder; TLC: $R_f$=0.35, methanol:chloroform (5:95); NMR: 0.84 (d,3, J=6.7), 0.85 (d,3, J=6.8), 1.17 (s,12), 1.7–1.8 (m,1), 2.15 (s,3), 2.66 (t,1), 4.48 (s,2), 7.46–7.55 (m,5), 8.29 (d,1, J=5), 8.82 (s,1), 9.54 (s,1); MS: m/z=469(M+1). Analysis for $C_{24}H_{33}BN_4O_5$: Calculated: C, 61.55; H, 7.10; N, 11.96; Found: C, 61.55; H, 7.23; N, 11.56.

EXAMPLE 14

2-[6-Oxo-2-phenyl-5-(4-pyridylmethoxycarbonylamino)-1,6-dihydro-1-pyrimidinyl]-N-[2-methyl-1-(4,4,5,5-tetramethyl-1,3,2-dioxaborolidine-2-yl)propyl]acetamide.

A solution of the product from Example 2 (0.50 g) and triethylamine (0.80 mL) in dichloromethane (5 mL) was cooled with an ice-water bath. To the solution was added triphosgene (0.17 g) in dichloromethane (1 mL) over 2 minutes. A dichloromethane (1 mL) wash of the addition syringe was also added to the reaction mixture. The mixture was stirred at ice bath temperature for 30 minutes. Solid 4-pyridinemethanol (0.38 g) was added in a single portion to the mixture. Stirring was continued at ice bath temperature for 90 minutes, and the solution was allowed to warm to room temperature overnight. The mixture was diluted with dichloromethane, washed (water), dried and evaporated to a brown foam (0.60 g). This material was purified by chromatography, with chloroform:methanol (50:1) as the eluent, to give the title compound (0.11 g) as a yellow solid; TLC: $R_f$=0.35, methanol:chloroform (5:95); NMR: 0.85 (d,6, J=7), 1.17 (s,1), 1.17–1.80 (m, 1), 2.68 (t,1), 4.48 (s,2), 5.24 (s,2), 7.44–7.56 (m,7), 8.28 (d,1, J=5.5), 8.47 (s,1), 8.58 (dd,2), 9.23 (s,1); MS: m/z=562(M+1).

EXAMPLE 15

2-[5-Cyclohexylaminosulfonylamino-2-(4-fluorophenyl)-6-oxo-1,6-dihydro-1-pyrimidinyl]-N-[2-methyl-1-(4,4,5,5-tetramethyl-1,3,2-dioxaborolidin-2-yl)propyl]acetamide To a solution of the product of Example 8 (0.33 g) and pyridine (0.30 mL) in tetrahydrofuran was added cyclohexylsulfamoyl chloride (0.22 g), and the mixture was allowed to stir for 2 hours. The solution was diluted with ethyl acetate, washed (water), and the ethyl acetate layer was dried and evaporated. Chromatography, with tetrahydrofuran:dichloromethane (gradient, 5:95 to 15:85) as the eluent, gave the title compound (0.3 g); TLC: Rf=0.7, tetrahydrofuran:dichloromethane (20:80); MS: m/z=606(M+1). Analysis for $C_{28}H_{41}BFN_5O_6S$: Calculated: C, 55.54; H, 6.82; N, 11.56; Found: C, 55.37; H, 6.92; N,11.49.

EXAMPLE 16

2-[2-(4-Fluorophenyl)-5-methylsulfonylamino-6-oxo-1,6-dihydro-1-pyrimidinyl]-N-[2-methyl-1-(4,4,5,5-tetramethyl-1,3,2-dioxaborolidin-2-yl)propyl] acetamide The product of Example 8 was subjected to a procedure similar to that described in Example 15 except substituting methanesulfonyl chloride for the cyclohexylsulfamoyl chloride used therein. Chromatography, with tetrahydrofuran:dichloromethane (gradient, 10:90 to 50:50) as the eluent, gave the title compound; TLC: $R_f$=0.4, tetrahydrofuran:dichloromethane (12:88); MS: m/z=523(M+1). Analysis for $C_{23}H_{32}BFN_4O_6S$: Calculated: C, 52.88; H, 6.17; N, 10.72; Found: C, 52.41; H, 6.05; N, 10.51.

EXAMPLE 17

2-[2-(4-Fluorophenyl)-5-methoxycarbonylamino-6-oxo-1,6-dihydro-1-pyrimidinyl]-N-[2-methyl-1-(4,4,5,5-tetramethyl-1,3,2-dioxaborolidin-2-yl)propyl] acetamide The product of Example 8 was subjected to a procedure similar to that described in Example 15 except substituting methylchloroformate for the cyclohexylsulfamoyl chloride used therein. Chromatography, with tetrahydrofuran:dichloromethane (gradient, 10:90 to 15:85) as the eluent, gave the title compound; TLC: $R_f$=0.4, tetrahydrofuran:dichloromethane (10:90); MS: m/z=503(M+1). Analysis for $C_{24}H_{32}BFN_4O_6$: Calculated: C, 57.38; H, 6.42; N, 11.15; Found: C, 57.45; H, 6.39; N, 11.05.

EXAMPLE 18

2-[2-(4-Fluorophenyl)-5-(2,6-dimethylpyrid-4-ylmethoxycarbonylamino)-6-oxo-1,6-dihydro-1-pyrimidinyl]-N-[2-methyl-1-(4,4,5,5-tetramethyl-1,3,2-dioxaborolidin-2-yl)propyl]acetamide The product of Example 8 was subjected to a procedure similar to that described in Example 14 except substituting 2,6-dimethyl-4-pyridinemethanol for the 4-pyridinemethanol used therein. Chromatography, with tetrahydrofuran:dichloromethane (gradient, 15:85 to 50:50) as the eluent, gave the title compound; TLC: $R_f$=0.5, tetrahydrofuran:dichloromethane (40:60); MS: m/z=608(M+1). Analysis for $C_{31}H_{39}BFN_5O_6$: Calculated: C,61.29; H,6.47; N, 11.53; Found: C, 61.26; H, 6.64; N, 11.21.

EXAMPLE 19

2-(5-Cyclohexylaminosulfonylamino-2-phenyl-6-oxo-1,6-dihydro-1-pyrimidinyl)-N-[2-methyl-1-(4,4,5,5-tetramethyl-1,3,2-dioxaborolidin-2-yl)propyl] acetamide The product of Example 2 was subjected to a procedure similar to that described in Example 15. Chromatography, with tetrahydrofuran:dichloromethane (gradient, 5:95 to 15:85) as the eluent, gave the title compound; TLC: $R_f$=0.7, tetrahydrofuran:dichloromethane (20:80); MS: m/z=588 (M+1). Analysis for $C_{28}H_{42}FBN_5O_6S$: Calculated: C, 57.24; H, 7.20; N, 11.92; Found: C, 57.28; H, 7.19; N, 11.75.

EXAMPLE 20

2-[2-(4-Aminophenyl)-5-cyclohexylaminosulfonylamino-6-oxo-1,6-dihydro-1-pyrimidinyl]-N-[2-methyl-1-(4,4,5,5-tetramethyl-1,3,2-dioxaborolidin-2-yl)propyl]acetamide The product from Example 20.c. was hydrogenated using a procedure similar to that described in Example 2. Chromatography, with tetrahydrofuran:dichloromethane, (gradient, 15:85 to 45:55) as the eluent, gave the title compound; TLC: $R_f$=0.2, tetrahydrofuran:dichloromethane (20:80); MS: m/z=603(M+1). Analysis for $C_{28}H_{43}BFN_6O_6S$: Calculated: C,55.81; H,7.19; N, 13.95; Found: C, 55.46; H, 7.12; N, 13.20.

The 4-nitrophenyl starting material was prepared as follows.

a. 2-[5-Benzyloxycarbonylamino-2-(4-nitrophenyl)-6-oxo-1,6-dihydro-1-pyrimidinyl]-N-[2-methyl-1-(4,4,5,5-tetramethyl-1,3,2-dioxaborolidin-2-yl)propyl]acetamide. 5-Benzyloxycarbonylamino-6-oxo-2-(4-nitrophenyl)-1,6-dihydro-1-pyrimidinylacetic acid (prepared as described in European Patent Application, Publication Number 528633) was coupled using a procedure similar to that described in Example 1. Chromatography, with tetrahydrofuran:dichloromethane (gradient, 4:96 to 10:90) as the eluent, gave the amide; TLC: $R_f$=0.5, tetrahydrofuran:dichloromethane (10:90); MS: m/z=606(M+1). It is noted that this is also a Compound of the invention.

b. 2-[5-Amino-2-(4-nitrophenyl)-6-oxo-1,6-dihydro-1-pyrimidinyl]-N-[2-methyl-1-(4,4,5,5-tetramethyl-1,3,2-dioxaborolidin-2-yl)propyl]acetamide. To a solution of 2-[5-benzyloxycarbonylamino-2-(4-nitrophenyl)-6-oxo-1,6-dihydro-1-pyrimidinyl]-N-[2-methyl-1-(4,4,5,5-tetramethyl-1,3,2-dioxaborolidin-2-yl)propyl]acetamide (3.2 g) and anisole (1.84 g) in dichloromethane (50 mL) was added trifluoromethanesulfonic acid (4.27 g), and the resulting mixture was stirred at 0° C. for 0.5 hour. The reaction was quenched by addition of a saturated aqueous solution of sodium bicarbonate, and the product was extracted into ethyl acetate. The combined extracts were washed (sodium bicarbonate, water), dried and evaporated. Chromatography, with tetrahydrofuran:dichloromethane (gradient, 15:85 to 40:60) as the eluent, gave the amine (1.7 g); TLC: $R_f$=0.1, tetrahydrofuran:dichloromethane (10:90); MS: m/z=472 (M+1). It is noted that this is also a Compound of the invention.

c. 2-[5-Cyclohexylaminosulfonylamino-2-(4-nitrophenyl)-6-oxo-1,6-dihydro-1-pyrimidinyl]-N-[2-methyl-1-(4,4,5,5-tetramethyl-1,3,2-dioxaborolidin-2-yl)propyl]acetamide. 2-[5-Amino-2-(4-nitrophenyl)-6-oxo-1,6-dihydro-1-pyrimidinyl]-N-[2-methyl-1-(4,4,5,5-tetramethyl-1,3,2-dioxaborolidin-2-yl)propyl]acetamide was subjected to a procedure similar to that described in Example 15. Chromatography, with tetrahydrofuran:dichloromethane (gradient, 5:95 to 15:85) as the eluent, gave the sulfamoyl compound; TLC: $R_f$=0.6, tetrahydrofuran:dichloromethane (20:80); MS: m/z=632(M+1). It is noted that this is also a Compound of the invention.

EXAMPLE 21

2-[5-Amino-2-(4-aminophenyl)-6-oxo-1,6-dihydro-1-pyrimidinyl]-N-[2-methyl-1-(4,4,5,5-tetramethyl-1,3,2-dioxaborolidin-2-yl)propyl]acetamide 2-[5-Amino-2-(4-nitrophenyl)-6-oxo-1,6-dihydro-1-pyrimidinyl]-N-[2-methyl-1-(4,4,5,5-tetramethyl-1,3,2-yl)dioxaborolidin-2-yl)propyl]acetamide was hydrogenated using a procedure similar to that described in in Example 2. Chromatography, with tetrahydrofuran:dichloromethane (gradient, 25:75 to 60:40) as the eluent, gave the title compound; TLC: $R_f$=0.2, tetrahydrofuran:dichloromethane (40:60); MS: m/z=442(M+1). Analysis for $C_{22}H_{32}BN_5O_4$: Calculated: C, 59.87; H, 7.31; N, 15.87; Found: C, 59.09; H, 7.12; N, 15.59.

FORMULAE

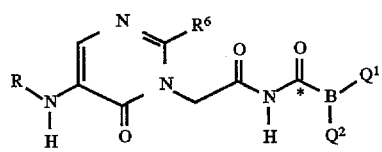  I

  IIa

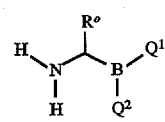  IIb

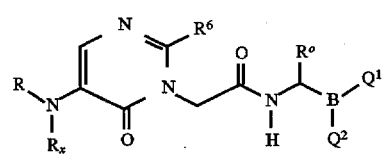  Vb

Scheme I

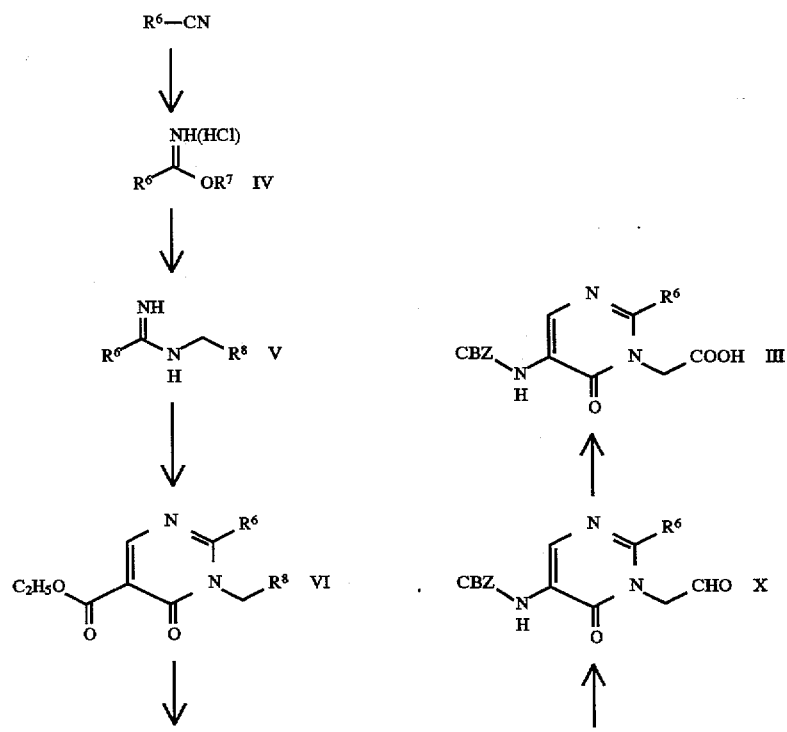

-continued
Scheme I

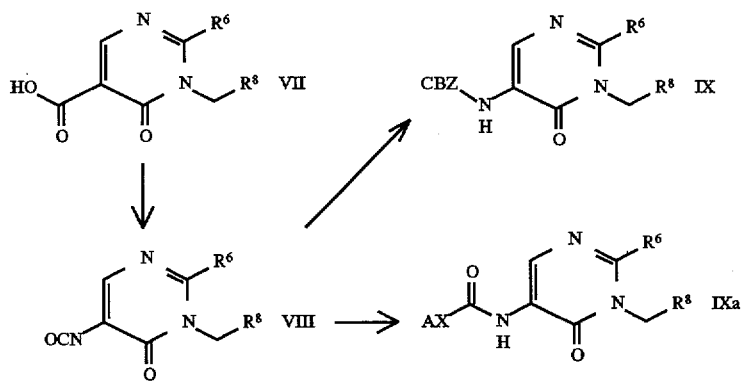

SCHEME II

XII → I, R = CBZ

↓

I, R = H

↓

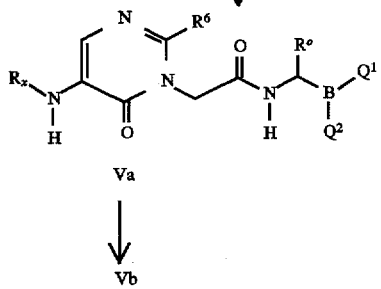
Va

↓

Vb

What is claimed is:
1. A compound of Formula I wherein

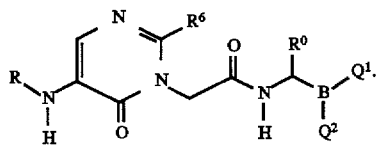
I $R^o$ is (1–5C)alkyl;
$R^6$ is (a) phenyl which may optionally bear one or more substituents selected from halogeno, (1–6C)alkyl, lower alkoxy, and amino;
(b)(1–5C)alkyl which has no tertiary carbon; or
(c) thienyl;
R is (a) hydrogen;
(b) an acyl group of the formula A. X. CJ where J is oxygen; X is oxy or a direct bond; and A is (1–6C) alkyl, benzyl, phenyl or pyridyl(1–3C)alkyl which may optionally bear one or more methyl groups; or
(c) a sulfonyl group of the formula D. W. SO₂ wherein D is (1–6C) alkyl or (3–6C)cycloalkyl and W is a direct bond or imino;
$Q^1$ and $Q^2$, which may be the same or different, is each hydroxy or $OR^7$, or when taken together form a moiety derived from a physiologically acceptable dihydroxy compound wherein said moiety is the residue derived from 2,3-butanediol, 2,3-dimethyl-2,3-butanediol, 1,3-propanediol, diethanolamine, catechol, (1R,2R,3S,5R)-(–)-pinanediol, (1S,2S,3R,5S-(+)-pinanediol, or 2,5-dimethylhexan-3,4-diol, wherein $R^7$ is (1–10C)alkyl, (3–10C)cycloalkyl, benzyl or phenyl in which benzyl or phenyl the ring may bear one or more halogeno, lower alkyl or lower alkoxy substituents;
or pharmaceutically acceptable salt thereof.

2. A compound as claimed in claim 5 wherein $R^o$ is methyl, ethyl, propyl, isopropyl or isobutyl; R is a sulfonyl group of the formula D. W. SO₂; W is a direct bond or imino; D is (1–3C)alkyl, (3–6C)cycloalkyl;

$R^6$ is isopropyl, thienyl or phenyl which may optionally bear one or two substituents selected from halogeno, (1–6C)alkyl, lower alkoxy, and amino;

$Q^1$ and $Q^2$ are each hydroxy, methoxy, ethoxy or isopropoxy; or $Q^1$ and $Q^2$, taken together, are the residue derived from 2,3-butanediol, 2,3-dimethyl-2,3-butanediol, 1,3-propanediol, diethanolamine, catechol, (1R,2R,3S,5R)-(–)-pinanediol, (1S,2S,3R, 5S)-(+)-pinanediol, or 2,5-dimethylhexan-3,4-diol.

3. A compound as claimed in claim 1 wherein $R^o$ is isopropyl; A is an acyl group of the formula A. X. CJ where J is oxygen; X is a direct bond or oxy; A is methyl, ethyl, phenyl, benzyl, or pyridylmethyl which may optionally bear one or more methyl groups.

4. A compound as claimed in claim 1, 2, or 3 wherein R is hydrogen, methoxycarbonyl, ethoxycarbonyl, isopropoxycarbonyl, benzyloxycarbonyl, 4-pyridylmethoxycarbonyl, 2,6-dimethylpyrid-4-ylmethoxycarbonyl, 2-pyridylmethoxycarbonyl, methylsulfonyl, acetyl, or cyclohexylaminosulfonyl.

5. A compound as claimed in any one of claims 1, 2, or 3 in which $R^6$ is 2-thienyl or phenyl in which the phenyl may bear one or two halogeno, methyl, methoxy, or tert-butoxy substituents.

6. A compound of formula Vb:

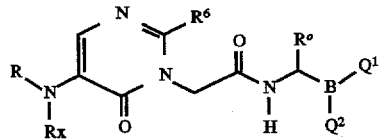
Vb wherein
R is (a) hydrogen;

(b) an acyl group of the formula A. X. CJ where J is oxygen; X is oxy or a direct bond; and A is (1–6C) alkyl, benzyl, phenyl or pyridyl(1–3C)alkyl which may optionally bear one or more methyl groups; or (c) a sulfonyl group of the formula D. W. $SO_2$ wherein D is (1–6C) alkyl or (3–6C)cycloalkyl; and W is a direct bond or imino;

$Q^1$ and $Q^2$, which may be the same or different, is each hydroxy or $OR^7$, or when taken together form a moiety derived from a physiologically acceptable dihydroxy compound wherein said moiety is the residue derived from 2,3-butanediol, 2,3-dimethyl-2,3-butanediol, 1,3-propanediol, diethanolamine, catechol, (1R,2R,3S,5R)-(−)-pinanediol, (1S,2S,3R,5S-(+)-pinanediol, or 2,5-dimethylhexan-3,4-diol, wherein $R^7$ is (1–10C)alkyl, (3–10C)cycloalkyl, benzyl or phenyl in which benzyl or phenyl the ring may bear one or more halogeno, lower alkyl or lower alkoxy substituents;

$R^o$ is (1–5C)alkyl;

$R^6$ is (a) phenyl which may optionally bear one or more substituents selected from halogeno, (1–6C)alky, lower alkoxy and amino;

(b) (1–5C)alkyl which has no tertiary carbon; or (c) thienyl; and

Rx is benzoyloxycarbonyl or trifluoroacetyl.

7. A compound as claimed in claim 5 wherein $R^6$ is phenyl, 4-fluorophenyl or 2-thienyl.

8. A compound selected from 2-(5-amino-6-oxo-2-phenyl-1,6-dihydro-1-pyrimidinyl)-N-[2-methyl-1-(4,4,5,5-tetramethyl-1,3,2-dioxaborolidin-2-yl)propyl]acetamide, 2-[5-cyclohexylaminosulfonylamino-2-(4-fluorophenyl)-6-oxo-1,6-dihydro-1-pyrimidinyl]-N-[2-methyl-1-(4,4,5,5-tetramethyl-1,3,2-dioxaborolidin-2-yl)propyl]acetamide, 2-(5-cyclohexylaminosulfonylamino-2-phenyl-6-oxo-1,6-dihydro-1-pyrimidinyl)-N-[2-methyl-1-(4,4,5,5-tetramethyl-1,3,2-dioxaborolidin-2-yl)propyl]acetamide, and 2-[2-(4-aminophenyl)-5-cyclohexylaminosulfonylamino-6-oxo-1,6-dihydro-1-pyrimidinyl]-N-[2-methyl-1-(4,4,5,5-tetramethyl-1,3,2-dioxaborolidin-2-yl)propyl]acetamide, or a pharmaceutically acceptable salt thereof.

9. A salt as claimed in claim 1 selected from (a) for an acidic compound of formula I, an alkalai metal salt, an alkaline earth metal salt, an aluminum salt, an ammonium salt, or a salt made from an organic base which affords a pharmaceutically acceptable cation; and (b) for a basic compound of formula I, an acid-addition salt made with an acid which provides a pharmaceutically acceptable anion.

10. A pharmaceutical composition comprising a compound as defined in claim 1, or a pharmaceutically acceptable salt thereof, and a pharmaceutically acceptable diluent or carrier.

11. A method of treating emphysema comprising administering to a human patient in need of treatment therefor an effective amount of a compound of claim 1.

* * * * *